United States Patent [19]
Johnston et al.

[11] 3,968,925
[45] July 13, 1976

[54] ANTI-REFLUX VALVE

[75] Inventors: Ray H. Johnston, Greenfield; Bryon L. Mather, Milwakee; Clark, James L., Whitefish Bay, all of Wis.

[73] Assignee: Plastronics, Inc., Milwaukee, Wis.

[22] Filed: May 12, 1975

[21] Appl. No.: 576,377

[52] U.S. Cl. .............................. 229/62.5; 128/2 F; 128/295; 137/525.3
[51] Int. Cl.² ........................................ F16K 15/14
[58] Field of Search ................. 128/2 F, 275, 295; 229/62.5; 137/525.3; 150/9

[56] References Cited
UNITED STATES PATENTS

| | | | |
|---|---|---|---|
| 2,378,613 | 6/1945 | Young | 137/525.3 |
| 3,330,100 | 7/1967 | Fesco | 229/62.5 X |
| 3,382,889 | 5/1968 | Heinz | 137/525.3 |
| 3,586,041 | 6/1971 | Monestere | 128/295 X |
| 3,626,980 | 12/1971 | Svensson | 128/295 X |

*Primary Examiner*—Robert G. Nilson
*Attorney, Agent, or Firm*—Michael, Best & Friedrich

[57] ABSTRACT

An anti-reflux valve mounted at the inlet port to the fluid collection chamber of a fluid collection bag and having a thin flexible valve element which is retained for limited floating movement over the inlet port and which flexes to permit flow of fluid into the collection chamber and which is moved against a valve seat surface surrounding the inlet port in response to fluid pressure inside of the collection chamber to thus prevent reflux of such fluid.

4 Claims, 4 Drawing Figures

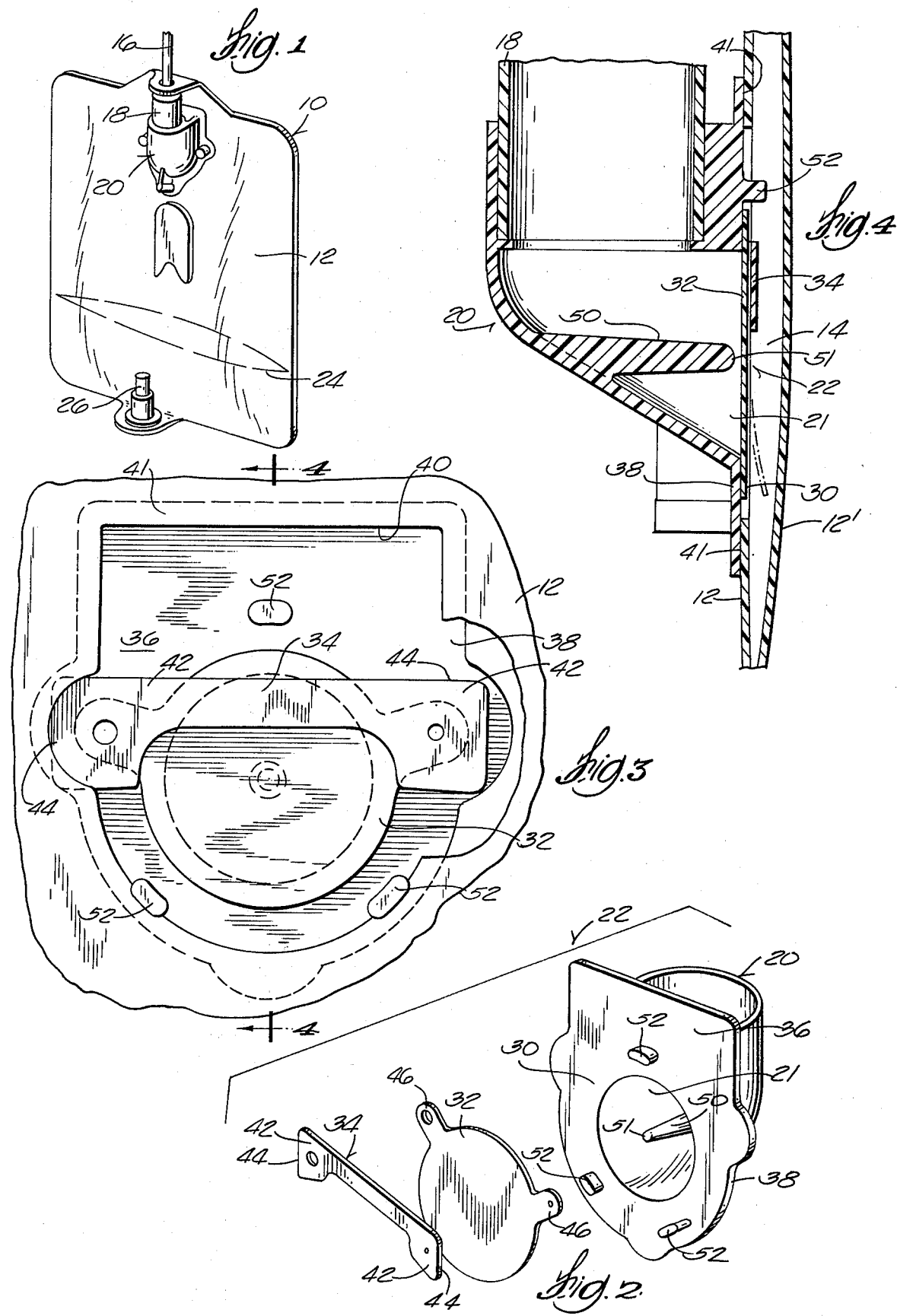

: 
ANTI-REFLUX VALVE

BACKGROUND OF THE INVENTION

The present invention pertains to the design of flexible urine drainage bags which are used for urinary catheterization of patients, and the invention resides in the provision of an effective anti-reflux valve for preventing reflux of urine (or air) from such bags towards the catheter when pressure is applied to the sidewall of the bag or when the bag is tipped.

The anti-reflux valve designs which have been proposed prior to the present invention have called for the use of a hinged check valve element, with the valve element being positioned at the inlet port communicating between the catheter and the drainage bag, and with the valve element being fixed to one side of the inlet port. The concept of using a fixedly mounted hinged valve element has not been practical because during the manufacture and subsequent sterilization of the drainage bag its components, i.e., the valve element and the valve seat tend to distort or to slightly deform, and such distortion or deformation may prevent the establishment of a uniform and consistent seal between the valve element and valve seat, and thus such deformation or distortion renders the operation of the anti-reflux valve unreliable.

SUMMARY OF THE INVENTION

The function and reliability of the anti-reflux valve embodying the present invention is not affected by the distortions and deformations encountered in the manufacture and sterilization of the drainage bag.

The valve element, which is made of a relatively thin and flexible material, is positioned in a limited floating and sliding relationship over the inlet port by a retaining member which extends over the exposed face of the valve element and is fixed at its ends to the inside surface of the flexible bag.

The valve element is of sufficiently larger size than the inlet port to completely cover the inlet port throughout the valve element's relative sliding or floating movement with respect to the inlet port, and, because of the absence of a fixed connection between the valve element and the inlet port or another component of the drainage bag, any distortion or deformation of the port or of other of the drainage bag components does not affect the sealing ability of the valve.

The valve element moves and flexes to permit passage of fluid from the catheter into the bag, and upon the creation of pressure within the bag, the flexible valve element is pressed against the valve seat on the inside face of the bag and thus effectively prevents relux into the catheter tube.

DESCRIPTION OF THE DRAWINGS

The presently commercial embodiment of the present invention is shown in the drawings in which:

FIG. 1 is a perspective view of the drainage bag;

FIG. 2 is an exploded view of the anti-reflux valve which is incorporated in the drainage bag shown on FIG. 1, and shows the valve seat element, the valve element and the retaining member of the anti-reflux valve;

FIG. 3 is a front view of the anti-reflux valve, when viewed from the inside of the drainage bag, with portions being broken away for the sake of illustration; and FIG. 4 is a cross-sectional side view taken on line 4—4 of FIG. 3, with valve element being shown in solid lines in a valve-closed position and, with the valve element being shown in broken lines in a valve-open position.

As illustrated in FIGS. 1 and 4, the drainage bag 10 is comprised of two generally rectangular, translucent and flexible sidewalls 12 and 12' which are bonded to each other at their edges to form an expandable collection chamber 14. The sidewalls of the commercial embodiment of the present invention are of vinyl or similar plastic material and, in the manufacture of the drainage bag, the edges are bonded to each other by industrial type radio frequency heaters (or other heat sealing equipment).

The drainage bag 10, when in use, is generally intended to be maintained on the vertical plane, as shown in FIG. 1. The catheter (not shown) is connected to a drainage tube 16, which in turn is fixed to connecting tube 18 of a connector member or drip chamber 20 of the drainage bag. Urine passes from the drainage tube 16 into the connecting member 20, through anti-reflux valve 22 into chamber 14. The urine is collected in the drainage bag, as shown at 24 in FIG. 1. A discharge tube 26 is provided at the bottom of the drainage bag and it may be connected to a suitable valve element (not shown) which is used in the emptying of the bag when desired.

The anti-reflux valve 22 is essentially comprised of three basic elements: a valve seat surface 30 surrounding a port 21, a flexible valve element 32, and a flexible retaining member 34 which retains the valve element in a limited floating position over the inlet port 21.

The valve seat surface 30 is formed on the inside planar surface of the flange portion 38 of connector member 20. The connector is of plastic material with flange 38 thereof extending over a cutout portion 40 in the sidewall 12 of bag 10 with flange 38 bonded to the outside wall of the sidewall 12 at the overlap 41.

The flexible and generally circular plastic valve element 32 is of a larger diameter than the inlet port 21 and it is retained in a floating and sliding relationship with respect to valve seat surface 30 over the inlet port by the plastic retaining member 34. Valve element 32 is preferably made from a relatively thin, semi-rigid plastic material such as mylar.

Retaining member 34 is in the form of a strip of plastic material (preferably vinyl) having a pair of enlarged end portions 42. Retaining member 34 extends over the upper portion of the inside face of valve element 32 and its end edges 44 of enlarged portions 42 are bonded to the inside surface 36 of the flange 38 to form a pair of retaining pockets beneath said end portions 42. The generally circular valve element is provided with two radially extending ears 46 which are slidably captured in the pockets formed under the end portions 42 of the retaining member and thus the valve element is retained for limited relative movement with respect to the valve seat surface surrounding inlet port 21. The surface area of the valve element is sufficiently large so that it will adequately cover the inlet port and properly engage the valve seat in any position the valve element 32 may assume in its limited transverse movement. The apertures shown in the illustrated valve element ears and in the end portions of the retaining member are provided for assembly purposes and have no relevance to the present invention.

When urine is drained into the cavity of the connecting member 20 it exerts pressure against the outside face of the valve element 32 and flexes it to a position as generally shown in broken lines in FIG. 4 to thereby permit the urine to pass into the collection chamber 14. If pressure is created within the drainage bag, as would be the case if it is squeezed, or if the urine within the bag is pressed against the inside face of the valve element 32, as would be the case if a full or partially full drainage bag is tipped, the force exerted against the inside face of the valve element 22 press the valve element against the valve seat 30 and thus prevent reflux of urine. A relatively rigid projection 50 is formed integrally on the inside wall of the cavity of the connecting member 20 and extends therefrom towards the central portion of valve element 32 with the end 51 thereof spaced a short distance from the outside face of element 32 when in its normally closed position as best shown in FIG. 4. Projector 50 serves to limit any tendency of valve element 32 to bulge outwardly into connector 20 through port 21 upon abrupt and/or excessive pressure being exerted on the inside face of element 32.

Finally it is noted that three inwardly extending projections 52 are provided on the flange 38 of connector 20 to prevent interference to the movement of the valve element by rear sidewall 12' of the bag 10.

From the foregoing it will be seen that with the reflux valve of this invention any tendency of the valve element and valve seat to become distorted with respect to each other during manufacture, sterilization or shipment will be substantially compensated for by the limited floating relationship between the valve element and the valve seat surface. Such floating retention of the valve element with respect to the valve seat is accomplished with a retaining structure which is relatively inexpensive to manufacture and simple to assemble, such arrangement permitting generally uni-directional flexing movement of the valve element in the desired manner to provide substantially unrestricted flow into the collection bag and to prevent any reflux of the liquid which has been collected inside the bag.

We claim:

1. An anti-reflux valve for a fluid drainage bag comprising:

a connector member fastened to a wall of said bag and having an inlet port communicating with the inside of said bag;

a valve seat surface on said connector member surrounding said inlet port thereof;

a flexible valve element mounted on said connector member on the inside of said bag and generally overlying said valve seat surface at said inlet port, said valve element being of generally circular shape and having two radially extending ears; and valve element retaining means for retaining said valve element on said connector member, said valve element retaining means including a retaining member in the form of a strip of plastic material having a pair of end portions with the edges of said end portions bonded to said connector member to form a pair of retaining pockets in which said radially extending ears of said valve element are slidably captured so that said valve element will be retained for limited relative transverse movement with respect to said valve seat surface, said valve element adapted for movement to an open position upon flow of fluid through said inlet port into the bag and further adapted for movement to a closed position into sealing engagement with said valve seat surface in response to fluid pressure exerted on said valve element from inside the bag.

2. An anti-reflux valve according to claim 1 in which said valve element is made of mylar.

3. An anti-reflux valve according to claim 1 in which there is a semi-rigid projection mounted in said connector member extending toward the central portion of said valve element with the end of said projection spaced a short distance from the face of said valve element when it is in its normally closed position, said projection serving to limit any tendency of the valve element to bulge outwardly into the connector member upon abrupt and/or excessive pressure being exerted on the inside face of the valve element.

4. An anti-reflux valve according to claim 3 in which said connector member has a plurality of inwardly extending projections formed thereon to prevent interference by the rear sidewall of the drainage bag to the movement of the valve element.

* * * * *

PO-1050
(5/69)

UNITED STATES PATENT OFFICE
CERTIFICATE OF CORRECTION

Patent No. 3,968,925            Dated July 13, 1976

Inventor(s) RAY H. JOHNSTON, BYRON L. MATHER and JAMES L. CLARK

It is certified that error appears in the above-identified patent and that said Letters Patent are hereby corrected as shown below:

Change the name of the Inventor: "Bryon"

to --Byron--.

Reverse the name of Inventor "Clark, James L."

to --James L. Clark--.

Column 1, line 55, change "relux" to --reflux--.

Signed and Sealed this

Fifth Day of October 1976

[SEAL]

Attest:

RUTH C. MASON            C. MARSHALL DANN
*Attesting Officer*            *Commissioner of Patents and Trademarks*